US009981238B2

(12) United States Patent
Castor

(10) Patent No.: US 9,981,238 B2
(45) Date of Patent: May 29, 2018

(54) APPARATUS AND METHODS FOR MAKING NANOSOMES LOADED WITH NUCLEIC ACID

(75) Inventor: Trevor Percival Castor, Arlington, MA (US)

(73) Assignee: Aphios Corporation, Woburn, MA (US)

(*) Notice: Subject to any disclaimer, the term of this patent is extended or adjusted under 35 U.S.C. 154(b) by 1003 days.

(21) Appl. No.: 13/216,079

(22) Filed: Aug. 23, 2011

(65) Prior Publication Data
US 2012/0052114 A1    Mar. 1, 2012

Related U.S. Application Data

(60) Provisional application No. 61/402,131, filed on Aug. 25, 2010.

(51) Int. Cl.
| | | |
|---|---|---|
| *B01J 13/04* | (2006.01) | |
| *A61K 9/127* | (2006.01) | |
| *A61K 31/713* | (2006.01) | |
| *B82Y 5/00* | (2011.01) | |
| *C12N 15/88* | (2006.01) | |

(52) U.S. Cl.
CPC .............. *B01J 13/04* (2013.01); *A61K 9/127* (2013.01); *A61K 9/1277* (2013.01); *A61K 31/713* (2013.01); *B82Y 5/00* (2013.01); *C12N 15/88* (2013.01)

(58) Field of Classification Search
CPC ...... A61K 9/1227; A61K 9/1277; B01J 13/02; B01J 13/04; B82Y 5/00
USPC ............................ 424/450; 264/4.1; 977/800
See application file for complete search history.

(56) References Cited

U.S. PATENT DOCUMENTS

| | | | | |
|---|---|---|---|---|
| 5,554,382 | A | * | 9/1996 | Castor ........................... 424/450 |
| 5,776,486 | A | * | 7/1998 | Castor et al. .................. 424/450 |
| 2004/0099976 | A1 | * | 5/2004 | Otake et al. ................... 264/4.1 |
| 2005/0025821 | A1 | * | 2/2005 | Harvie et al. ................. 424/450 |

OTHER PUBLICATIONS

Castor, Trevor P. "Phospholipid Nanosomes" Current Drug Delivery Oct. 2005; 2(4): 329-340.*
5X siRNA Buffer (Thermo Scientific 2010) Accessed via the internet Mar. 18, 2015.*

* cited by examiner

Primary Examiner — Walter D. Griffin
Assistant Examiner — Marc C Howell
(74) Attorney, Agent, or Firm — McCarter & English, LLP; Elizabeth A. Hanley; Mei Bai

(57) ABSTRACT

Embodiments of the present invention are directed to an apparatus and methods for making nucleic acid loaded nanosomes. One embodiment of the present invention directed to an apparatus comprises a first containment means for containing a mixture of an aqueous solution of nucleic acid and a phospholipid solution with a supercritical, critical or near critical fluid. The apparatus further comprises injection means in fluid communication with said first containment means for receiving the mixture and releasing the mixture as a stream into a decompression liquid. The apparatus further comprises a decompression vessel in fluid communication with the injection means for holding a decompression liquid and receiving the mixture as a stream. The stream forms one or more nanosomes loaded with a nucleic acid in the decompression liquid.

15 Claims, 1 Drawing Sheet

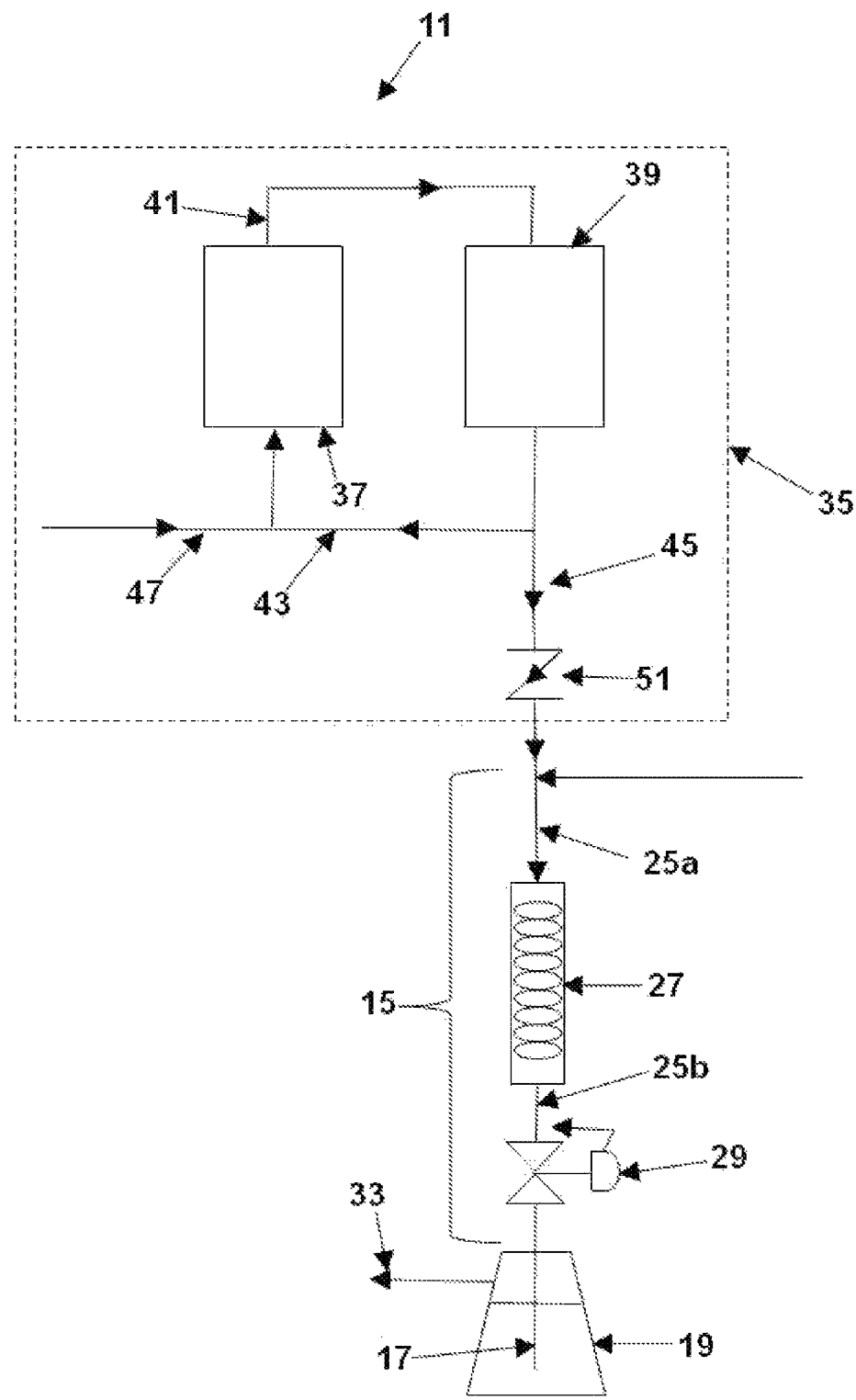

APPARATUS AND METHODS FOR MAKING NANOSOMES LOADED WITH NUCLEIC ACID

CROSS-REFERENCE TO RELATED APPLICATIONS

This application is a continuation of U.S. provisional application Ser. No. 61/402,131 filed Aug. 23, 2010. This application claims priority to such provisional application and incorporates by reference the disclosure therein.

FEDERAL SUPPORT

This invention was not supported with Federal funds.

FIELD OF THE INVENTION

The present invention pertains to the nanoencapsulation of siRNA and other biologies in phospholipid nanosomes for the improved delivery of siRNA and other biologies to targeted disease human or animal organs and human or animal cells and apparatus and methods for making the same.

BACKGROUND OF THE INVENTION

The present invention relates to small interfering ribonucleic acids (hereinafter referred to as siRNAs). siRNAs are small double stranded RNA, usually 20 to 25 nucleotides in length which bind to other nucleic acids and interfere with or silence expression events. siRNAs are used to study expression and disease states involving expression events. siRNAs have utility controlling of expression at the cellular level to treat disease. However, siRNA have been limited by difficulty in placing the RNA in the cell or cells.

It is difficult to make liposomes of a size that permits absorbtion or other delivery of siRNAs to the interior of cells. Liposomes having a diameter measured in nanometers, from about 10 to 500 nanometers, are referred to as nanosomes. Nanosomes have potential as a delivery vehicle for siRNAs. However, it is difficult to make nanosomes with consistent and high load of an agent such as siRNAs. Processes for loading an agent do not necessarily permit the recycling of agent not incorporated into the liposome resulting in a loss of the agent and higher costs of manufacture.

SUMMARY OF THE INVENTION

Embodiments of the present invention are directed to an apparatus and methods for making nucleic acid loaded nanosomes. One embodiment of the present invention directed to an apparatus comprises a first containment means for containing a mixture of an aqueous solution of nucleic acid and a phospholipid solution with a supercritical, critical or near critical fluid. The apparatus further comprises injection means in fluid communication with said first containment means for receiving the mixture and releasing the mixture as a stream into a decompression liquid. The apparatus further comprises a decompression vessel in fluid communication with the injection means for holding a decompression liquid and receiving the mixture as a stream. The stream forms one or more nanosomes loaded with a nucleic acid in the decompression liquid.

As used above, the term "nucleic acid" refers to deoxyribonucleic acids (DNA) and ribonucleic acid (RNA). These nucleic acids may have any sequence desired. One embodiment of the present invention is directed to siRNAs.

Embodiments of the present invention feature supercritical, critical and near critical fluids. A compound becomes critical at conditions that equal both its critical temperature and critical pressure. A compound becomes supercritical at conditions that equal or exceeds both its critical temperature and critical pressure. As used herein, the term near critical is used to denote a compound that approaches one or both critical temperature and critical pressure, but is not a critical or supercritical fluid. These parameters are intrinsic thermodynamic properties of all sufficiently stable pure compounds and mixtures. Carbon dioxide, for example, becomes a supercritical fluid at conditions that equal or exceed its critical temperature of 31.1° C. and its critical pressure of 72.8 atm (1,070 psig). As a supercritical fluid, normally gaseous substances, such as carbon dioxide, become dense phase fluids that have been observed to exhibit greatly enhanced solvating power.

At a pressure of 3,000 psig (20 atm) and a temperature of 40° C., carbon dioxide has a density of approximately 0.8 g/cc and exhibits properties similar to those of a nonpolar solvent such as hexane, having a dipole moment of zero Debyes. A supercritical, critical or near critical fluid has a wide spectrum of solvation power, as its density is strongly dependent upon temperature and pressure. Temperature changes of tens of degrees or pressure changes by tens of atmospheres can change a compound's solubility in a supercritical, critical or near critical fluid by an order of magnitude or more. Temperature and pressure allow the fine-tuning of solvation properties and the fractionation of mixed solutes. The selectivity of nonpolar supercritical, critical and near critical fluids can be influenced by the addition of compounds known as modifiers, entrainers and co-solvents. These modifiers are typically more polar, such as acetone, ethanol and methanol.

One embodiment of the present invention features a circulation loop in fluid communication with the first containment means. The circulation loop is for forming the phospholipid solution with a supercritical, critical or near critical fluid. One embodiment of a circulation loop has a solids vessel for holding a phospholipid and forming a suspension of phospholipid and a supercritical, critical or near critical fluid. Another embodiment of a circulation loop has a mixing chamber in communication with said solids vessel for receiving the suspension of phospholipid and a supercritical, critical or near critical fluid and forming the phospholipid solution with a supercritical, critical or near critical fluid.

One embodiment of a circulation loop has return means in fluid communication with the mixing chamber and the solids vessel for returning a suspension or solution of a phospholipid with a supercritical, critical or near critical fluid from the mixing chamber to the solids vessel to increase the phospholipid content of the suspension of phospholipids and a supercritical, critical or near critical fluid. One embodiment of a circulation loop has one or more pumps to move the suspension or solution of a phospholipid and a supercritical, critical or near critical fluid through the solids vessel and mixing chamber.

A preferred circulation loop is in fluid communication with a source of supercritical, critical or near critical fluid.

One embodiment of the apparatus features a first containment means in fluid communication with a siRNAs source. For example, the siRNAs source holds a siRNAs in a buffer. One preferred buffer is a low ionic strength buffer.

One embodiment of the apparatus features containment means in the form of one or more conduits, vessels and an inline mixer.

A further embodiment of the present invention, directed to a method of forming a nucleic acid loaded nanosome comprises the step of forming a mixture of an aqueous solution of a nucleic acid and a phospholipid solution with a supercritical, critical or near critical fluid in a first containment means. Next, the method comprises the step of directing the mixture to injection means in fluid communication with the first containment means and releasing the mixture as a stream into a decompression liquid held in a decompression vessel in fluid communication with the injection means. And, the method comprises the step of forming one or more nanosomes loaded with a nucleic acid in the decompression liquid.

One method features a nucleic acid which is a siRNAs.

One embodiment of the method features the further step of forming the phospholipid solution with a supercritical, critical or near critical fluid in a circulation loop. The circulation loop is in fluid communication with the first containment means. One circulation loop has a solids vessel for holding a phospholipid and forming a suspension of phospholipid and a supercritical, critical or near critical fluid. One circulation loop has a mixing chamber in communication with the solids vessel for receiving the suspension of phospholipid and a supercritical, critical or near critical fluid and forming the phospholipid solution with a supercritical, critical or near critical fluid.

One circulation loop has return means in fluid communication with the mixing chamber and the solids vessel for returning a suspension or solution of a phospholipid with a supercritical, critical or near critical fluid from the mixing chamber to the solids vessel to increase the phospholipid content of the suspension of phospholid and a supercritical, critical or near critical fluid. The method further comprising the step of circulating said suspension or solution of a phospholipid with a supercritical, critical or near critical fluid. A preferred circulation loop has one or more pumps to move the suspension or solution of a phospholipid and a supercritical, critical or near critical fluid through the solids vessel and mixing chamber. One embodiment of the present method features a circulation loop in fluid communication with a source of supercritical, critical or near critical fluid.

One embodiment features a first containment means in fluid communication with a siRNA source. A preferred siRNA source holds a siRNA in a buffer. And, a preferred buffer is a low ionic strength buffer. One method comprises the step of forming a buffered solution of a siRNA.

One embodiment of the method features containment means having one or more conduits, vessels and inline mixers.

A further embodiment of the present invention is directed to, as an article of manufacture, a nanosome comprising a phospholipid and a siRNA with trace amounts of a low ionic strength buffer.

These and other features and advantages of the present invention will be apparent to those skilled in the art upon viewing the FIGURE which is described briefly below and upon reading the detailed description that follows.

BRIEF DESCRIPTION OF THE DRAWING

The FIGURE depicts a schematic representation of an apparatus embodying features of the present invention.

DETAILED DESCRIPTION OF THE INVENTION

Embodiments of the present invention will be described in detail as an apparatus and methods for making nucleic acid loaded nanosomes in which the nucleic acid is siRNA. The description represents the best mode known to the inventor and is subject to further alteration and modification without departing from the teachings herein. Therefore, the present discussion should not be considered limiting.

Turning now to FIG. 1, an apparatus having features of the present invention, generally designated by the numeral 11, is depicted. Apparatus 11 comprises three major elements: a first containment means 15, injection means 17 and decompression vessel 19. Apparatus 11 can be made of any size depending on the amount of nanosomes desired from the processes. Materials for making elements of the apparatus 11 are rigid with strength to contain pressures and temperatures used to maintain supercritical, critical or near critical conditions. A preferred material is metals such as stainless steel.

The first containment means 15 is comprised of conduits 25*a* and 25*b*, in-line mixer 27 and a pressure regulator 29. First containment means is for containing a mixture of an aqueous solution of nucleic acid and a phospholipid solution with a supercritical, critical or near critical fluid. Other embodiments of the first containment means 15 may comprise additional features such as vessels [not shown]. The conduit 25*a* receives an aqueous solution of nucleic acid; and, the conduit receives a phospholipid solution with a supercritical, critical or near critical fluid. The aqueous solution and the phospholipid solution are directed into the in-line mixer to form a mixture. The mixture is directed into conduit 25*b* and maintained at an appropriate pressure by the pressure regulator 29.

Injection means 17 is in fluid communication with the first containment means 15 via conduit 25*b* for receiving the mixture and releasing the mixture as a stream into a decompression liquid. Injection means 17 comprises one or more nozzles having opening for releasing the mixture which appear as bubbles in a decompression liquid described in greater detail in a later discussion. The size of the openings and the flow of the mixture influence the size of the nanosomes formed. One embodiment of injection means 17 is a 10-mil (internal diameter of 0.25 mm or 250 micron) capillary injection nozzle. Larger internal diameter 316 stainless steel capillary tubes can be used to manufacture larger particle sizes. Impingement nozzles (Bete Fog Nozzle, Inc., Greenfield, Mass.) can also be used.

Decompression vessel 19 is in fluid communication with the injection means 17. Decompression vessel 19 holds a decompression liquid and openings of injection means are held under the decompression liquid to allow the mixture to be released as a stream with the gas of the supercritical, critical or near critical fluid bubbling to the surface. Decompression vessel 19 has an opening [not shown] or vent 33 for venting or discharging the gas. The stream forms one or more nanosomes loaded with a nucleic acid in the decompression liquid.

Apparatus 11 further comprises a circulation loop 35. Circulation loop 35 comprises a solids vessel 37, a mixing vessel 39, a feed conduit 41, a return conduit 43 and an exit conduit 45. Circulation loop 35 is in fluid communication with a source of gas at a pressure and temperature consistent with a supercritical, critical or near critical fluid or such gas and the phospholipids are brought to such conditions in the circulation loop 35. As depicted, circulation loop 35 receives a gas through source conduit 47 under supercritical, critical or near critical temperatures and pressure at a junction or "T" in return conduit 43. Those skilled in the art will immediately recognize that source conduit 45 may be introduced at any point in circulation loop 35.

Circulation loop 35 is in fluid communication the first containment means 15 via exit conduit 45. Exit conduit 45 has a valve 51 to direct fluids through the exit conduit and into the first containment means 15 or through the return conduit 43. The circulation loop 35 is for forming a phospholipid solution with a supercritical, critical or near critical fluid. The solids vessel 37 holds a phospholipid and forms a suspension or solution of phospholipid and a supercritical, critical or near critical fluid. Mixing chamber 39 is in fluid communication with solids vessel 37 via the feed conduit 41 for receiving the suspension of phospholipid and a supercritical, critical or near critical fluid and forming the phospholipid solution with a supercritical, critical or near critical fluid.

Return means in the form of return conduit 43 is in fluid communication with the mixing chamber 39 and the solids vessel 37 for returning a suspension or solution of a phospholipid with a supercritical, critical or near critical fluid from the mixing chamber 39 to the solids vessel 37. The returning fluid removes more phospholipid from the solids vessel 37 to increase the phospholipid content of the solution or suspension of phospholipid and a supercritical, critical or near critical fluid.

Preferably, the circulation loop 35 has one or more pumps [not shown] known in the art to move the suspension or solution of a phospholipid and a supercritical, critical or near critical fluid through the solids vessel 37, mixing chamber 39, return conduit 43 and feed conduit 41.

Embodiments of the present method will now be described with respect to the operation of the apparatus 11. The method will be described with respect forming a nucleic acid loaded nanosome. A mixture of an aqueous solution of a nucleic acid and a phospholipid solution with a supercritical, critical or near critical fluid is formed in a first containment means 15. The mixture is directed to injection means 17 in fluid communication with the first containment means 15. Injection means 17 releases the mixture as a stream into a decompression liquid held in a decompression vessel 19. One or more nanosomes loaded with a nucleic acid is formed in the decompression liquid.

In a further step, the phospholipid solution with a supercritical, critical or near critical fluid is formed in a circulation loop 35. Phospholipids held in solids vessel 37 are carried as a solution or suspension of phospholipid and a supercritical, critical or near critical fluid via feed conduit 41 to mixing vessel 39 to forming the phospholipid solution with a supercritical, critical or near critical fluid.

Return means in the form of return conduit 43 in fluid communication with the mixing chamber and the solids vessel returns a suspension or solution of a phospholipid with a supercritical, critical or near critical fluid from the mixing chamber to the solids vessel to increase the phospholipid content of the suspension of phospholipids and a supercritical, critical or near critical fluid. The fluids are circulated to increase the phospholipid content of the solution ultimately leaving the circulation loop 35 via exit conduit 45.

Article of manufacture made by apparatus 11 and the methods herein described are nanosome comprising a phospholipid and a nucleic acid with trace amounts of a low ionic strength buffer. One preferred nucleic acid is siRNA.

Features of the present invention are further exemplified in the Example which follows.

EXAMPLES

Experiments were conducted in the constant pressure co-injection mode in which a lipid rich-supercritical, critical or near critical fluid solution stream and a siRNA rich-buffer stream were co-injected into a buffer. Embodiments of the present invention achieve particle sizes in the 100 nm to 200 nm range. Embodiments of the present invention achieve siRNA encapsulation efficiency in the 40% to 100% range with some of the most significant parameters being the pH of the injection siRNA molecule and the co-injection ratios. Embodiments achieve 95 to 100% total siRNA recovery efficiency.

The highest total siRNA encapsulation of 95.9% was obtained in with a decompression fluid comprising 10% sucrose buffer in which the co-injection ratio was 1.0 and the co-injection pH was 4.0.

The highest relative siRNA encapsulation of 89.5% was obtained with a decompression fluid comprising 10% sucrose buffer in which the co-injection ratio was 3.0 and the co-injection pH of 4.0.

A particle size of 106 nm was obtained with a co-injection ratio of 9.0.

A high ionic strength formulation buffer consisting of PBS, sodium citrate and sodium chloride at pH −7.0 resulted in a lower relative encapsulation efficiency compared to a similar co-injection run with 10% sucrose formulation buffer that resulted in an 82% siRNA relative encapsulation efficiency.

Results to date suggest that siRNA encapsulation and recovery efficiencies are functions of both feed and formulation pH. The impact of feed and product pH on siRNA recovery and encapsulation efficiencies for a co-injection ratio of 3.0. Data suggests relative encapsulation efficiency plateaus at pHs between 4 and 5. Total siRNA recovery efficiency appears to increase in a linear fashion with pH over the 3.5 to 7.0 range tested.

While this invention has been particularly shown and described with references to specific embodiments, it will be understood by those skilled in the art that various changes in form and details may be made therein without departing from the spirit and scope of the invention as defined by the appended claims.

The invention claimed is:

1. A method of forming a siRNA loaded nanosome comprising the steps of:
   a. forming a mixture of an aqueous solution of a siRNA and a phospholipid solution with a supercritical, critical or near critical fluid in a first containment means comprising an inline mixer;
   b. directing said mixture to an injector in fluid communication with said first containment means and having an opening(s) for releasing said mixture as a stream into a decompression liquid held in a decompression vessel in fluid communication with said injector;
   c. forming one or more nanosomes loaded with the siRNA in said decompression liquid; wherein said one or more nanosomes encapsulate the siRNA with an encapsulation efficiency of 95 to 100% with said decompression liquid comprising about 10% sucrose buffer in which co-injection ratios of said phospholipid solution with the supercritical, critical or near critical fluid to said aqueous solution of siRNA are between 1.0 and 9.0 and pH of said aqueous solution of siRNA is about 4.0.

2. The method of claim 1 further comprising the step of forming said phospholipid solution with the supercritical, critical or near critical fluid in a circulation loop, said circulation loop in fluid communication with said first containment means.

3. The method of claim 2 wherein said circulation loop has a solids vessel for holding a phospholipid and forming said phospholipid solution with the supercritical, critical or near critical fluid.

4. The method of claim 3 wherein said circulation loop has a mixing chamber in communication with said solids vessel for receiving said supercritical, critical or near critical fluid and forming said phospholipid solution with the supercritical, critical or near critical fluid.

5. The method of claim 2 wherein said circulation loop is in fluid communication with a source of the supercritical, critical or near critical fluid.

6. The method of claim 4 wherein said circulation loop has return means in fluid communication with said mixing chamber and said solids vessel for returning said phospholipid solution with the supercritical, critical or near critical fluid from said mixing chamber to said solids vessel to increase the phospholipid content of said phospholipid solution with the supercritical, critical or near critical fluid, said method further comprising the step of circulating said supercritical, critical or near critical fluid over said phospholipid in the solids vessel.

7. The method of claim 6 wherein said circulation loop has one or more pumps to move said phospholipid solution with the supercritical, critical or near critical fluid through said solids vessel and mixing chamber.

8. The method of claim 1 wherein said first containment means is in fluid communication with a siRNA source.

9. The method of claim 8 wherein said siRNA source holds the siRNA in a buffer.

10. The method of claim 9 wherein said buffer is a low ionic strength buffer.

11. A method of forming siRNA loaded nanosomes comprising the steps of:
 a. providing a device having a first containment means, a circulation loop in fluid communication with said first containment means, an injector in fluid communication with said first containment means, and a decompression vessel holding said injector and in fluid communication with said injector, wherein said first containment means comprises an inline mixer; wherein said circulation loop comprises a mixing chamber and a solids vessel; and wherein said decompression vessel holds a decompression liquid;
 b. forming a phospholipid solution with a supercritical, critical or near critical fluid in said circulation loop, wherein a phospholipid is held in said solids vessel and mixed and dissolved by said supercritical, critical or near critical fluid as said supercritical, critical or near critical fluid is circulated in said circulation loop and flows through said mixing chamber forming a dissolved phospholipid that increases in the concentration of the phospholipid in time and circulation to reach a final concentration of the phospholipid in said supercritical, critical or near critical fluid;

c. forming a mixture of an aqueous solution of a siRNA and said phospholipid solution with the supercritical, critical or near critical fluid in the first containment means in which said phospholipid solution is at said final concentration;

d. directing said mixture to said injector in fluid communication with said first containment means and releasing said mixture as a stream into said decompression liquid held in said decompression vessel;

e. forming one or more nanosomes loaded with the siRNA in said decompression liquid; wherein said one or more nanosomes encapsulate the siRNA with a total siRNA recovery efficiency of 95 to 100% with said decompression liquid comprising about 10% sucrose buffer in which co-injection ratios of said phospholipid solution with the supercritical, critical or near critical fluid to said aqueous solution of siRNA are between 1.0 and 9.0 and pH of said aqueous solution of the siRNA is about 4.0.

12. The method of claim 11 wherein said first containment means is in fluid communication with a siRNA source.

13. The method of claim 11 wherein said siRNA source holds the siRNA in a buffer.

14. The method of claim 13 wherein said buffer is a low ionic strength buffer.

15. The method of claim 11 wherein said one or more nanosomes encapsulates the siRNA with an encapsulation efficiency of 40-100%.

* * * * *

UNITED STATES PATENT AND TRADEMARK OFFICE
CERTIFICATE OF CORRECTION

PATENT NO.         : 9,981,238 B2                                    Page 1 of 1
APPLICATION NO.    : 13/216079
DATED              : May 29, 2018
INVENTOR(S)        : Trevor Percival Castor It is certified that error appears in the above-identified patent and that said Letters Patent is hereby corrected as shown below:

In the Claims

Column 8, Claim number 13, Line number 37, delete "11" and replace with --12--.

Signed and Sealed this
Eighteenth Day of September, 2018

Andrei Iancu
*Director of the United States Patent and Trademark Office*